United States Patent
Govari

(10) Patent No.: US 9,351,657 B2
(45) Date of Patent: May 31, 2016

(54) CARDIAC ACTIVITY VISUALIZATION WITH FREQUENCY DISCRIMINATION

(71) Applicant: BIOSENSE WEBSTER (ISRAEL), LTD., Yokneam (IL)

(72) Inventor: Assaf Govari, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 97 days.

(21) Appl. No.: 13/946,044

(22) Filed: Jul. 19, 2013

(65) Prior Publication Data
US 2015/0025351 A1    Jan. 22, 2015

(51) Int. Cl.
| A61B 5/00 | (2006.01) |
| A61B 5/044 | (2006.01) |
| A61B 5/042 | (2006.01) |
| A61B 5/04 | (2006.01) |
| A61B 5/0452 | (2006.01) |
| A61B 17/00 | (2006.01) |

(52) U.S. Cl.
CPC ............ *A61B 5/044* (2013.01); *A61B 5/04014* (2013.01); *A61B 5/0422* (2013.01); *A61B 5/0452* (2013.01); *A61B 5/6869* (2013.01); *A61B 5/7253* (2013.01); *A61B 5/7475* (2013.01); *A61B 5/04017* (2013.01); *A61B 2017/00053* (2013.01)

(58) Field of Classification Search
None
See application file for complete search history.

(56) References Cited

U.S. PATENT DOCUMENTS

| 4,649,482 | A | | 3/1987 | Raviv et al. |
| 5,046,504 | A | * | 9/1991 | Albert et al. ................ 600/509 |
| 5,546,951 | A | * | 8/1996 | Ben-Haim ................... 600/515 |
| 5,738,096 | A | * | 4/1998 | Ben-Haim ................... 600/407 |
| 6,226,542 | B1 | * | 5/2001 | Reisfeld ...................... 600/407 |
| 6,301,496 | B1 | * | 10/2001 | Reisfeld ...................... 600/407 |
| 7,918,793 | B2 | * | 4/2011 | Altmann et al. ............. 600/437 |
| 8,478,389 | B1 | * | 7/2013 | Brockway et al. ........... 600/509 |
| 2007/0038251 | A1 | | 2/2007 | Pachon Mateos et al. |
| 2007/0049817 | A1 | * | 3/2007 | Preiss et al. ................. 600/407 |
| 2008/0188765 | A1 | * | 8/2008 | Stolarski et al. ............ 600/518 |
| 2008/0214945 | A1 | | 9/2008 | Koertge et al. |
| 2009/0306641 | A1 | | 12/2009 | Govari et al. |
| 2011/0190625 | A1 | | 8/2011 | Harlev et al. |
| 2012/0184863 | A1 | | 7/2012 | Harlev et al. |
| 2012/0184865 | A1 | | 7/2012 | Harlev et al. |

FOREIGN PATENT DOCUMENTS

| WO | 2007/146864 A2 | 12/2007 |
| WO | 2008/035070 A2 | 3/2008 |

OTHER PUBLICATIONS

EP Search Report EP 14 17 7768 Dated Dec. 10, 2014.
Berntsen, R.F. et al. Evaluation of Spatiotemporal Organization of Persistent Atrial Fibrillation With Time and Frequency Domain Measures in Humans. Europace, vol. 11, No. 3, 2009, pp. 316-323.

(Continued)

*Primary Examiner* — Brian T Gedeon
(74) *Attorney, Agent, or Firm* — Louis J. Capezzuto

(57) ABSTRACT

A method includes measuring electrical activity at multiple points on a surface of a heart of a patient. User input indicative of a spectral slice selected from a frequency band is received. Respective levels of the electrical activity within the selected spectral slice are calculated. The calculated levels are displayed on a map of the heart.

11 Claims, 4 Drawing Sheets

(56) References Cited

OTHER PUBLICATIONS

Bin, He et al. A High Resolution Cardiac Mapping System. IEEE 10.1109/IEMBS.1992.5761252, pp. 812-814.

Ciaccio E.J. et al. Temporal Stability in the Spectral Representation of Complex Fractionated Atrial Electrograms. Pacing and Clinical Electrophysiology, 2014, Vol. 37, No. 1, pp. 79-89.

* cited by examiner

CARDIAC ACTIVITY VISUALIZATION WITH FREQUENCY DISCRIMINATION

FIELD OF THE INVENTION

The present invention relates generally to electro-anatomical mapping, and particularly to methods and systems for visualizing electro-cardio signals.

BACKGROUND OF THE INVENTION

Various techniques are known in the art for spatially mapping cardiac signals in a heart cavity. For example, U.S. Patent Application Publication 2011/0190625, whose disclosure is incorporated herein by reference, describes a non-contact cardiac mapping method that includes: (i) inserting a catheter into a heart cavity having an endocardium surface, the catheter including multiple, spatially distributed electrodes; (ii) measuring signals at the catheter electrodes in response to electrical activity in the heart cavity with the catheter spaced from the endocardium surface; and (iii) determining physiological information at multiple locations of the endocardium surface based on the measured signals and positions of the electrodes with respect to the endocardium surface. Related systems and computer programs are also disclosed.

U.S. patent application Publication 2009/0306641, whose disclosure is incorporated herein by reference, describes a method for providing an electro-anatomical representation of a patient's heart which includes measuring signals at one or more electrodes at multiple positions in the patient's heart cavity over a time period including multiple heart beat cycles, at least some of the signals being in response to electrical activity in the patient's heart cavity. An algorithm is applied to one or more specific signals of the measured signals to determine a triggering event in the specific signal. The signals measured at the one or more electrodes are synchronized by the computer with one another according to a heartbeat cycle based on the triggering event. The electro-anatomical representation of the patient's heart is generated by the computer based on the synchronized measured signals and positions of the catheter electrodes.

SUMMARY OF THE INVENTION

An embodiment of the present invention described herein provides a method including measuring electrical activity at multiple points on a surface of a heart of a patient. User input indicative of a spectral slice selected from a frequency band is received. Respective levels of the electrical activity within the selected spectral slice are calculated. The calculated levels are displayed on a map of the heart.

In some embodiments, measuring the electrical activity includes contacting the surface of the heart with a catheter at the multiple points and measuring electro-cardiac signals at the respective multiple points using the catheter. In other embodiments, calculating the levels of the electrical activity within the selected spectral slice includes computing a frequency spectrum of the electro-cardiac signals at the respective multiple points. In yet other embodiments, displaying the levels includes measuring respective positions of the catheter while the catheter touches the points, and displaying the levels at the respective positions on the map of the heart.

In some embodiments, receiving the user input includes receiving the selected spectral slice from a slide bar input device. In other embodiments, displaying the calculated levels includes assigning the levels respective colors, and coloring the map of the heart in accordance with the colors. In yet other embodiments, displaying the levels includes receiving a digitized three-dimensional image of the heart, correlating the calculated levels to the multiple points on the image, and displaying the map of the correlated calculated levels and the image on a user display.

There is additionally provided herein, in accordance with an embodiment of the present invention, an apparatus including an interface and a processor. The interface is configured to receive user input indicative of a spectral slice selected from a frequency band. The processor is configured to measure electrical activity at multiple points on a surface of a heart of a patient, to calculate respective levels of the electrical activity within the selected spectral slice, and to display the calculated levels on a map of the heart.

The present invention will be more fully understood from the following detailed description of the embodiments thereof, taken together with the drawings in which:

DETAILED DESCRIPTION OF EMBODIMENTS

Overview

Patient electro-cardiac signals are sometimes monitored during therapeutic and cardiac procedures. Electro-cardiac signals can be sampled locally using catheters which are navigated into the heart cavity. Electro-anatomical mapping systems use the local electro-cardiac signals in conjunction with heart map images, to identify local regions in the heart where various pathologies may be present. For example, regions with the high frequency of the local electro-cardiac signals are indicative with heart tissue associated with fibrillation and other heart dysfunctions.

Embodiments of the present invention described herein include improved methods and systems for visualizing electro-cardiac activity. In the disclosed embodiments, a frequency discrimination system visualizes the level of electro-cardiac activity for a particular spectral slice that is selected by an operator. In this manner, regions of associated with a particular frequency slice of the electro-cardiac signal is spatially mapped onto an image of the heart.

In an embodiment, the operator selects a desired frequency of the electro-cardiac signal. In response, the system is configured to display the level of electrical activity across the heart surface, restricted to that frequency. Different amplitudes of electrical activity at the desired frequency may be represented by different colors, for example. The operator may select the desired spectral slice using a suitable control in real-time. As the operator modifies the selected spectral slice, the visualization changes accordingly. The operator may observe the change of coloring for different spectral slices, and use this form of visualization technique to identify various heart pathologies.

For example, areas of the heart that are associated with fibrillation and/or fractionated electrograms may exhibit a predominance of high-frequency activity, in comparison with areas of normal electrical activity. Direct visualization of the frequency distribution of electrical activity over the area of a heart chamber may therefore be useful in identifying and planning treatment of arrhythmias.

System Description

Figure 1:
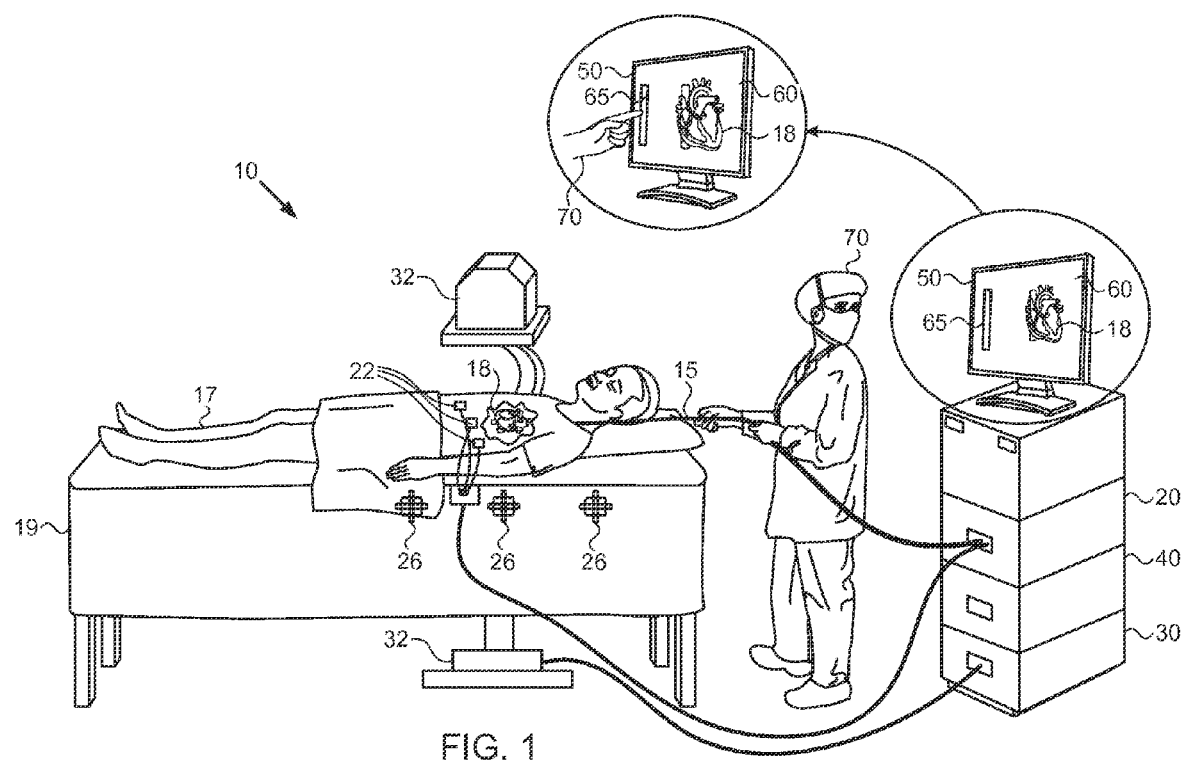
FIG. 1 is a schematic, pictorial illustration of an electro-anatomical mapping system, in accordance with an embodiment of the present invention.

FIG. 1 is a schematic, pictorial illustration of an electro-anatomical mapping system 10, in accordance with an embodiment of the present invention. A catheter 15 is percutaneously inserted into a living body 17 of a patient lying on a gurney 19. Catheter 15 is connected to an electro-anatomical mapping and navigation unit (EMNS) 20 in system 10. Catheter 15 is navigated into a heart 18 of the patient. An example of a catheter navigation and tracking system (EMNS 20) is the CARTO system (Biosense Webster, Diamond Bar, Calif.).

In an embodiment, one or more electro-cardiac signal (ECS) probe sensors 22 are attached to the surface of patient body 17 near heart 18 in order to receive electro-cardiac signals. Probe sensors 22 are connected to EMNS 20. The signals acquired by sensors 22 may be used, for example, for gating the visualization to a particular phase of the electro-cardiogram (ECG) cycle.

One or more magnetic field generators 26 create a magnetic field through the body of the patient, which induce signals in position sensors within the distal tip of catheter 15 (not shown in the diagram). The induced signals are used by EMNS 20 to track the position of catheter 15 in heart 18.

The local electro-cardiac signals are sampled when the distal tip of catheter 15 locally contacts the heart tissue. The position of the catheter distal tip during tracking is displayed to an operator 70 on an output display 60 on a monitor 50, and recorded along with the local electro-cardiac signals. The known position of the distal tip of catheter 15 during sampling of the electro-cardiac signals enables EMNS 20 to record the electrical activity at the positions of multiple points on the surface of the heart cavity in patient 17.

In some embodiments, although not necessarily, an imaging system (IS) 30 is used to obtain the image of the heart. Imaging system 30 comprises an imaging source 32, which may use magnetic resonance imaging (MRI), X-ray computed tomography (CT), fluoroscopy or any suitable imaging technique to obtain the heart image. The image of the heart is then digitized and stored in IS 30.

An electro-cardio signal frequency discrimination system (ESFDS) 40 receives the digitized heart image in IS 30 and the local electro-cardiac signals obtained from EMNS 20. (In alternative embodiments, IS 30 is omitted, and both position information and local electrical activity levels are received from EMNS 20.) ESFDS 40 correlates the heart image data and the local electro-cardiac signals data at multiple points on the surface of the heart cavity.

In some embodiments, ESFDS 40 performs a frequency transformation so as to obtain the frequency spectrum of the electro-cardiac data at each point on the heart surface. Thus, the ESFDS forms a three-dimensional (3D) spatial map of the heart with the local frequency spectrum electro-cardiac signal at the multiple points.

ESFDS 40 is configured to receive a user input from operator 70, indicating a particular spectral slice whose amplitude is to be visualized. Operator terminal 50 comprises display 60 and a user input device, such as a touch slide bar 65. The operator can choose the desired spectral slice (frequency range) of the electro-cardiac signal by moving his finger on frequency slide bar 65 as shown in the inset of FIG. 1. ESFDS 40 calculates the respective levels of the electrical activity within the selected spectral slice, e.g., the voltage levels of the electro-cardiac signals. The calculated levels of the selected spectral slice can be viewed on the map of heart 18 and viewed on display 60 by operator 70. Alternatively to slide bar 65, ESFDS 40 may use any other suitable control to receive the spectral slice selection from operator 70.

The exemplary system 10 shown in FIG. 1 is for visual clarity and not by way of limitation of the embodiments of the present invention. In some embodiments, system 10 may comprise both imaging system 30 and EMNS 20 which can be operated during the same diagnostic session. In other embodiments, system 10 may comprise only ESFDS 40 and EMNS 20 to provide electro-anatomical mapping. Further alternatively, ESFDS 40 may use imaging data that has been previously acquired and uploaded to the ESFDS. In yet other embodiments, system 10 may be used in conjunction with other therapeutic procedures, for example, where catheter 15 is also configured to perform cardiac tissue ablation.

Figure 2:
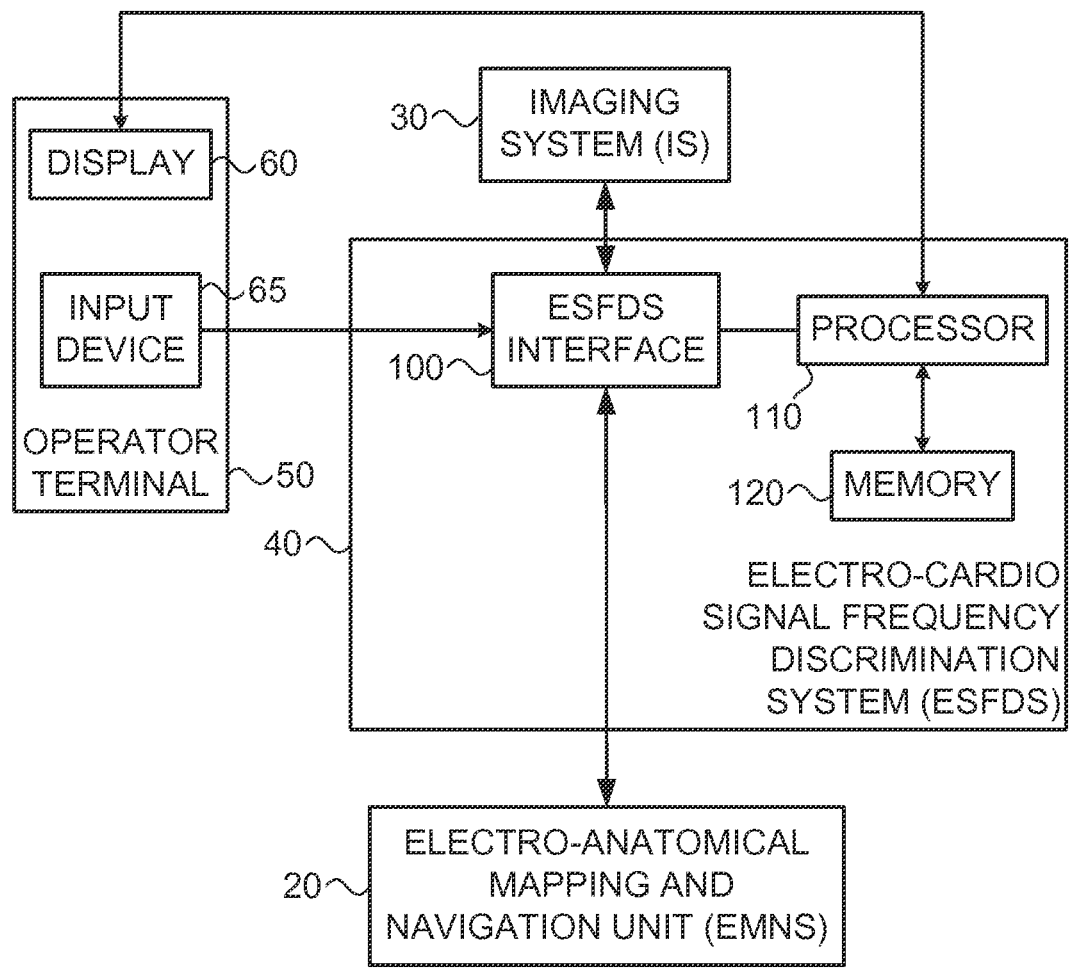
FIG. 2 is a block diagram that schematically illustrates an electro-cardio signal frequency discrimination system, in accordance with an embodiment of the present invention.

FIG. 2 is a block diagram that schematically illustrates electro-cardio signal frequency discrimination system 40, in accordance with an embodiment of the present invention. Local ECS data from electro-anatomical mapping and navigation unit (EMNS) 20, and heart image map data from imaging system (IS) 30 are sent to ESFDS 40 via an ESFDS interface 100. ESFDS interface 100 also receives the frequency slice selected by operator 70 from user input device 65 on operator terminal 50 (e.g., touch slide bar 65).

ESFDS 40 further comprises a processor 110 and a memory 120. Processor 110 receives the local ECS data and the heart image map, calculates the frequency spectrum of the local ECS data, and correlates the processed data to the heart image map. The correlated map of the heart image with the processed local ECS data is stored in memory 120. Processor 110 also outputs the calculated levels (e.g., voltage amplitude) of the electro-cardiac signal activity at the frequency slice set by input device 65. The respective levels are spatially mapped onto an image of the heart previously acquired by IS 30 at multiple points along the surface of the heart and outputted to display 60.

In some embodiments, ESFDS 40 may be a separate unit. In other embodiments, ESFDS 40 may be integrated within EMNS 20, IS 30, or in any other suitable configuration to perform the functions described herein. Some elements of ESFDS 40 may be implemented in hardware, e.g., in one or more Application-Specific Integrated Circuits (ASICs) or Field-Programmable Gate Arrays (FPGAs). Additionally or alternatively, some ESFDS elements can be implemented using software, or using a combination of hardware and software elements. In some embodiments, processor 110 comprises a general-purpose computer, which is programmed in software to carry out the functions described herein. The software may be downloaded to the computer in electronic form, over a network, for example, or it may, alternatively or additionally, be provided and/or stored on non-transitory tangible media, such as magnetic, optical, or electronic memory.

Electro-Cardiac Frequency Discrimination

The frequency spectrum of local electro-cardio signals sampled by catheter 15 at multiple points along the surface of the heart gives an indication of local heart dysfunction. For example, areas of the heart that exhibit high frequency electro-cardiac activity may indicate fibrillation or fractionated electro-cardiograms in comparison to other areas of normal electrical activity.

Figure 3A:
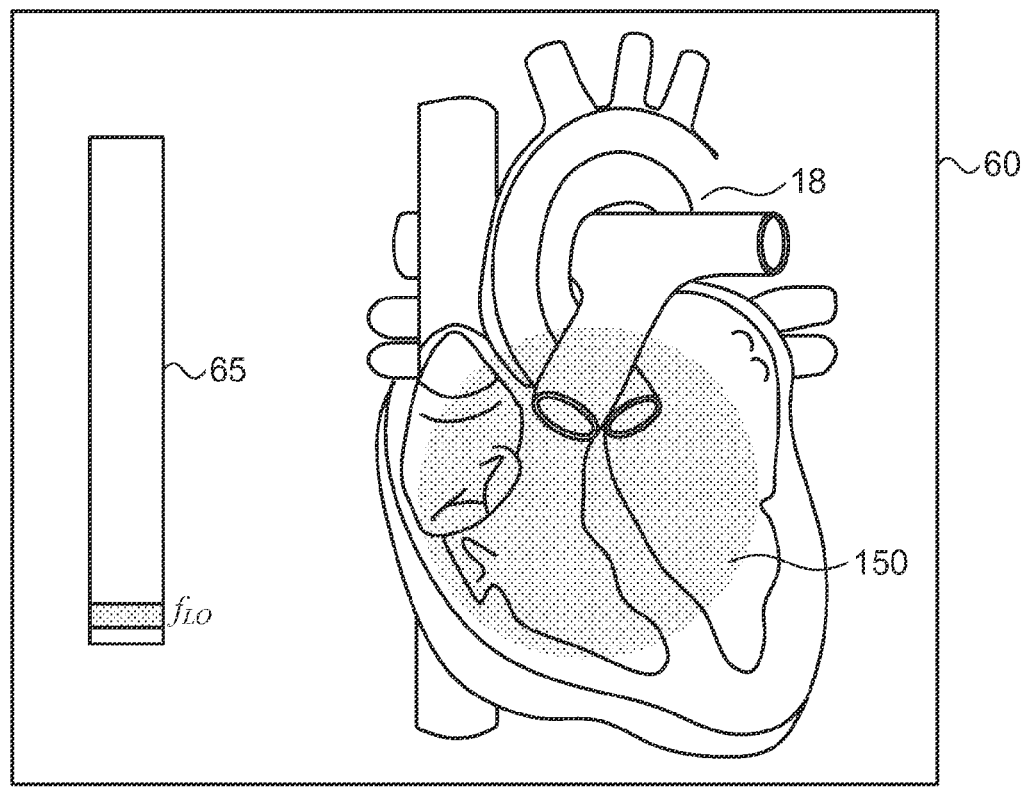
FIGS. 3A and 3B are diagrams illustrating a visualization of electro-cardiac activity on an image of the heart, in accordance with an embodiment of the present invention.
Figure 3B:
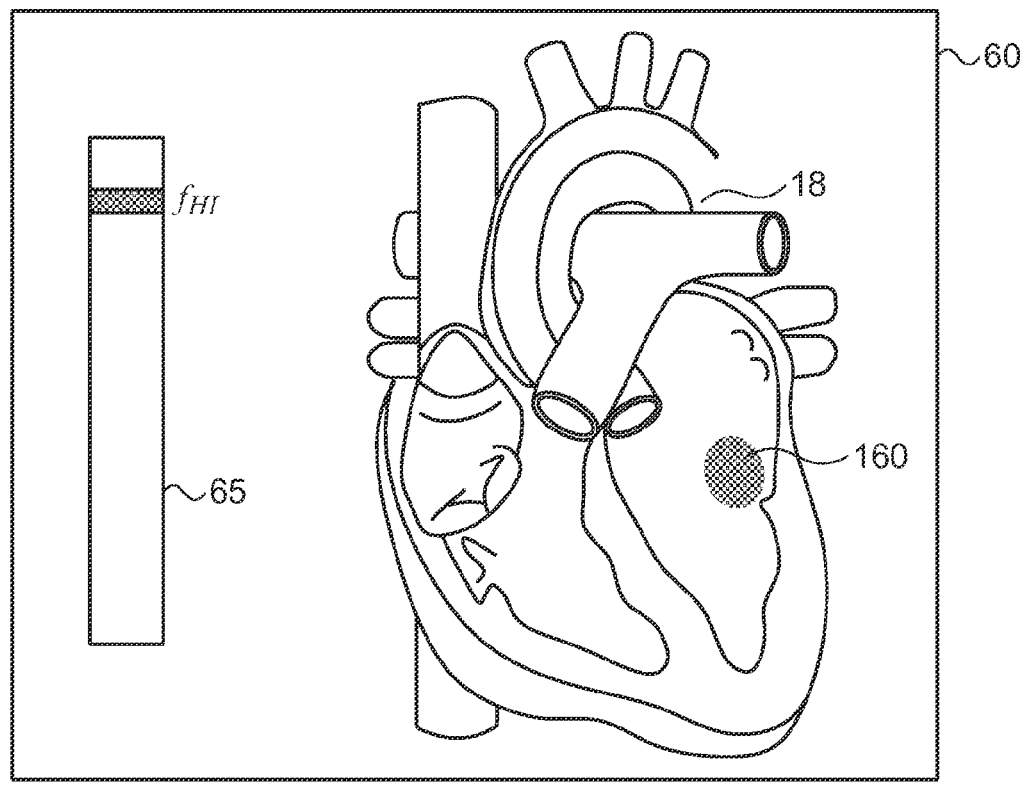

FIGS. 3A and 3B are diagrams illustrating electro-cardiac signal mapping onto an image of the heart, in accordance with an embodiment of the present invention. In FIG. 3A, operator 70 decides to view the voltage amplitude of the electro-cardiac signal in a spectral slice having a low frequency denoted $f_{LO}$. To do so, operator 70 moves touch slide bar 65 on display 60 to select low frequency $f_{LO}$ spectral slice within the frequency band assessable by slide bar 65. In response, ESFDS 40 displays an image of the heart and a region 150 of heart 18 with electrical activity at frequency $f_{LO}$. Since lower frequency electro-cardio signals are associated with normal heart function, the electro-cardiac signals with a low frequency $f_{LO}$ component are present over most of the surface of the heart cavity as shown in FIG. 3A.

In order to assess localized heart dysfunction, in FIG. 3B operator 70 selects a spectral slice on slide bar 65 with a high frequency, $f_{HI}$, a frequency that is known to be associated with arrhythmias as described previously. In this case, operator 70 can view a localized damaged region 160 of heart 18 on display 60.

Slide bar 65 is typically configured to allow operator 70 to choose a spectral slice within a range of frequencies obtained in the frequency transformation of the electro-cardiac signal data. The lower and upper edges of the slide bar are thus configured to be the lowest and highest frequencies, respectively, from the transformation. In an embodiment, the lowest and highest frequencies that are displayed are 0.01 Hz and 300 Hz, respectively. The frequency range of 10-25 Hz is typically the band of interest used for identifying heart dysfunction in accordance with the embodiments described herein.

In some embodiments, ESFDS 40 assigns respective colors to the respective levels of the electro-cardiac signal in the spectral slice (e.g., voltage amplitude). These colors are then overlaid on the 3D map of the heart on display 60 and viewed by operator 70. In this form of visualization, regions of high activity at the selected frequency will be marked with a certain color, while regions of low activity at the selected frequency will be marked with a different color. Alternatively, ESFDS 40 may use any other suitable form of visualization.

Operator 70 may raster his finger on the slide bar to change the selected frequency quickly in order to view and observe any changes in position of localized damaged region 160. Changes in the distribution of electrical activity across the heart surface from one frequency to another can be a useful diagnostic input.

In some embodiments, system 10 may also comprise ESFDS 40 along with an additional unit to perform therapeutic procedures, such as ablation therapy. Catheter 15 can be navigated to region 160 not only to sample the local electro-cardiac signal but also to ablate the damaged tissue identified by ESFDS 40. This method restores the heart to normal function immediately after diagnosis of heart dysfunction by ESFDS 40 during the same medical procedure.

In some embodiments, the electro-cardio signal voltage waveforms obtained by EMNS 20 at various points on the surface of the heart are converted to a frequency spectrum by processor 110, for example, by the use of Fast Fourier Transform (FFT) computations. In other embodiments, the calculated levels (e.g., voltage amplitude) of the frequency spectrum of the electro-cardiac signals at multiple points along the surface of the heart cavity pre-correlated to the acquired image of the heart is uploaded and stored in memory 120. The pre-correlated data may be acquired prior to the diagnostic procedure.

Figure 4:
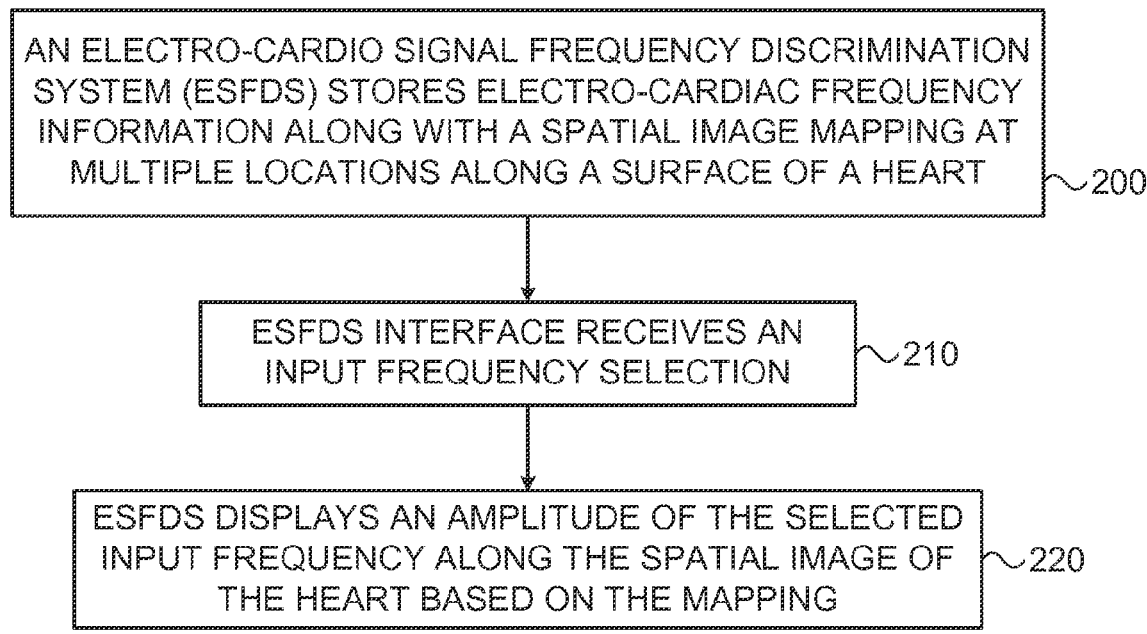
FIG. 4 is a flow chart that schematically illustrates a method for visualizing electro-cardiac activity with frequency discrimination, in accordance with an embodiment of the present invention.

FIG. 4 is a flow chart that schematically illustrates a method for visualizing cardiac electrical activity, in accordance with an embodiment of the present invention. In a storing step 200, electro-cardio signal frequency discrimination system (ESFDS) 40 stores electro-cardiac frequency information along with a spatial image mapping at multiple locations on a surface of heart 18 in memory 120.

In a receiving step 210, ESFDS interface 100 receives a spectral slice selection from input device 65. The selection defines the spectral slice of the electro-cardiac signal frequency band that operator 70 wants to view spatially mapped onto the image of heart 18 on display 60. In a displaying step 220, ESFDS 40 displays the amplitude of the selected input frequency along the spatial image of the heart based on the mapping obtained from step 200.

Although the embodiments described herein mainly address using frequency discrimination in cardiac diagnostic procedures, the methods and systems described herein can also be used in other applications, such as in electro-encephalography (EEG).

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A method, comprising:
   measuring electrical activity at multiple points on a surface of a heart of a patient using one or more sensors attached to a body of the patient positioned near the heart for receiving electro-cardiac signals from the heart;
   percutaneously inserting a catheter into a chamber of the heart and measuring local electrical activity at multiple points on the surface of the heart with the catheter;
   tracking a position of the catheter in the heart at each of the multiple points on the surface of the heart and recording the local electrical activity at each of the multiple points on the surface of the heart using a mapping and navigation system operatively connected to the catheter;
   receiving heart image data as well as the measured local electrical activity and the position of the catheter recorded at each of the multiple points on the surface of the heart and user input indicative of a spectral slice selected from a frequency band of the electro-cardiac signals from the heart by the one or more sensors attached to the body of the patient;
   calculating respective levels of the electrical activity within the selected spectral slice; and
   displaying the calculated levels of the electrical activity within the selected spectral slice on a 3-D map of the heart on a display.

2. The method according to claim 1, wherein calculating the levels of the electrical activity within the selected spectral slice comprises computing a frequency spectrum of the electro-cardiac signals at the respective multiple points.

3. The method according to claim 1, wherein displaying the levels comprises measuring respective positions of the catheter while the catheter touches the points, and displaying the levels at the respective positions on the map of the heart.

4. The method according to claim 1, wherein receiving the user input comprises receiving the selected spectral slice from a slide bar input device.

5. The method according to claim 1, wherein displaying the calculated levels comprises assigning the levels respective colors, and coloring the map of the heart in accordance with the colors.

6. An apparatus, comprising:
a display;
one or more sensors attached to a body of a patient positioned near a heart for receiving electro-cardiac signals from the heart;
a catheter for percutaneous insertion into a chamber of a heart, the catheter being used to measure local electrical activity at multiple points on a surface of the heart;
a mapping and navigation system operatively connected to the catheter and configured to track a position of the catheter in the heart at each of the multiple points on the surface of the heart and to record the local electrical activity at each of the multiple points on the surface of the heart;
an image of the heart, the image being digitized as heart image data
an electro-cardio signal frequency discrimination system comprising:
(i) an interface, which is configured to receive the heart image data as well as the measured local electrical activity and the position of the catheter recorded at each of the multiple points on the surface of the heart, the interface also configured to receive user input indicative of a spectral slice selected from a frequency band of the electro-cardiac signals from the heart by the one or more sensors attached to the body of the patient;
(ii) a processor operatively connected to the interface, the processor configured to measure local electrical activity at multiple points on the surface of the heart of the patient, to calculate respective levels of the electrical activity within the selected spectral slice, and to display the calculated levels of the electrical activity within the selected spectral slice on a 3-D map of the heart on the display.

7. The apparatus according to claim 6, wherein the processor is configured to calculate the levels of the electrical activity within the selected spectral slice by computing a frequency spectrum of the electro-cardiac signals at the respective multiple points.

8. The apparatus according to claim 6, wherein the interface is configured to receive respective positions of the catheter that are measured while the catheter touches the points, and wherein the processor is configured to display the levels at the respective positions on the map of the heart.

9. The apparatus according to claim 6, wherein the interface is configured to receive the selected spectral slice from a slide bar input device.

10. The apparatus according to claim 6, wherein the processor is configured to display the calculated levels by assigning the levels respective colors and coloring the map of the heart in accordance with the colors.

11. The apparatus according to claim 6, wherein the interface is configured to receive a digitized three-dimensional image of the heart, and wherein the processor is configured to correlate the calculated levels to the multiple points on the image, and to display the map of the correlated calculated levels and the image on a user display.

* * * * *